(12) United States Patent
Karlsson et al.

(10) Patent No.: US 9,228,953 B2
(45) Date of Patent: Jan. 5, 2016

(54) TESTING SYSTEM AND METHOD FOR TESTING

(71) Applicant: Calmark Sweden AB, Karlstad (SE)

(72) Inventors: Mathias Karlsson, Karlstad (SE); Sofia Hiort Af Ornaes, Trosa (SE)

(73) Assignee: Calmark Sweden AB, Karlstad (SE)

( * ) Notice: Subject to any disclaimer, the term of this patent is extended or adjusted under 35 U.S.C. 154(b) by 92 days.

(21) Appl. No.: 14/356,708

(22) PCT Filed: Nov. 22, 2012

(86) PCT No.: PCT/SE2012/051293
§ 371 (c)(1),
(2) Date: May 7, 2014

(87) PCT Pub. No.: WO2013/077803
PCT Pub. Date: May 30, 2013

(65) Prior Publication Data
US 2014/0329262 A1 Nov. 6, 2014

Related U.S. Application Data

(60) Provisional application No. 61/614,554, filed on Mar. 23, 2012.

(30) Foreign Application Priority Data

Nov. 23, 2011 (SE) ...................... 1151116

(51) Int. Cl.
*G01N 33/52* (2006.01)
*G01N 21/75* (2006.01)
(Continued)

(52) U.S. Cl.
CPC ................ *G01N 21/75* (2013.01); *G01N 21/78* (2013.01); *G01N 33/726* (2013.01); *G01N 33/50* (2013.01); *G01N 2021/1765* (2013.01); *G01N 2021/1776* (2013.01); *G01N 2430/00* (2013.01)

(58) Field of Classification Search
CPC ... G01N 33/50; G01N 2430/00; G01N 21/75; G01N 21/78; G01N 33/726; G01N 2021/1765; G01N 2021/1776
See application file for complete search history.

(56) References Cited

U.S. PATENT DOCUMENTS 5,408,535 A 4/1995 Howard, III et al.
6,441,898 B1 8/2002 Markart
(Continued)

FOREIGN PATENT DOCUMENTS

CN 101329280 A 12/2008
JP 2007-101482 A 4/2007
(Continued)

OTHER PUBLICATIONS

United States Patent and Trademark Office, Office Action for U.S. Appl. No. 14/358,317, Oct. 6, 2014, 8 pages, USA.
(Continued)

*Primary Examiner* — Dennis M White
(74) *Attorney, Agent, or Firm* — Alston & Bird LLP

(57) ABSTRACT

This invention relates to a testing system for assessing the level of a biochemical marker, comprising a disposable device (2) with a sample inlet (4) and a at least one visible detection compartment (5A, 5B), arranged with composition including a chemical means (Y) for direct detection of said biochemical marker, wherein said composition also includes an inhibitor (Z) arranged to first detection compartment (5A) being arranged to block the biochemical marker up to a certain concentration.

20 Claims, 2 Drawing Sheets

(51) Int. Cl.
  *G01N 21/78* (2006.01)
  *G01N 33/72* (2006.01)
  *G01N 33/50* (2006.01)
  *G01N 21/17* (2006.01)

(56) References Cited

U.S. PATENT DOCUMENTS

| | | |
|---|---|---|
| 7,267,799 B1 | 9/2007 | Borich et al. |
| 2005/0203353 A1 | 9/2005 | Ma et al. |
| 2006/0008914 A1 | 1/2006 | Scheuringer |
| 2006/0222567 A1 | 10/2006 | Kloepfer et al. |
| 2006/0292039 A1 | 12/2006 | Iida |
| 2008/0213744 A1 | 9/2008 | Karlsson et al. |
| 2012/0106811 A1 | 5/2012 | Chen et al. |

FOREIGN PATENT DOCUMENTS

| | | | |
|---|---|---|---|
| JP | 2008-116234 A | 5/2008 | |
| WO | WO 03/044474 A1 | 5/2003 | |
| WO | WO 2006/107666 A2 | 10/2006 | |
| WO | WO 2010/095394 A1 | 8/2010 | |
| WO | WO 2011/040874 A1 | 4/2011 | |
| WO | WO 2012/061650 A2 | 5/2012 | |

OTHER PUBLICATIONS

European Patent Office, Extended European Search Report for Application No. 12851190.4, May 21, 2015, 6 pages, Germany.

Japan Patent Office, Notification of Reason for Refusal for Application No. 2014-543450, May 19, 2015, 3 pages, Japan.

United States Patent and Trademark Office, Office Action for U.S. Appl. No. 14/358,317, Mar. 17, 2015, 7 pages, USA.

State Intellectual Property Office of the P.R.C., Office Action for Application No. 201280065735.1, Sep. 16, 2015, 6 pages, China.

International Searching Authority, International Search Report for International Application No. PCT/SE2012/051292, Feb. 13, 2013, 5 pages, Swedish Patent and Registration Office, Sweden.

International Searching Authority, International Search Report for International Application No. PCT/SE2012/051293, Feb. 13, 2013, 5 pages, Swedish Patent and Registration Office, Sweden.

International Searching Authority, Written Opinion for International Application No. PCT/SE2012/051292, Feb. 13, 2013, 4 pages, Swedish Patent and Registration Office, Sweden.

International Searching Authority, Written Opinion for International Application No. PCT/SE2012/051293, 5 pages, Swedish Patent and Registration Office, Sweden.

TESTING SYSTEM AND METHOD FOR TESTING

CROSS REFERENCE TO RELATED APPLICATIONS

This application is a National Stage Application, filed under 35 U.S.C. §371, of International Application No. PCT/SE2012/051293, filed Nov. 22, 2012, which claims priority to and the benefit of Swedish Application No. 1151116-9, filed Nov. 23, 2011, and U.S. Provisional Application No. 61/614,554, filed Mar. 23, 2012; the contents of all of which are hereby incorporated by reference in their entirety.

BACKGROUND

1. Related Field

Testing system for assessing the level of a biochemical marker, comprising a disposable device with a sample inlet and a at least one visible detection compartment, arranged with composition including a chemical means for direct detection of said biochemical marker.

2. Description of Related Art

Biochemical analysis of biochemical markers from blood and other body fluids are probably the most commonly performed diagnostic test besides clinical examination of a patients. Biochemical analysis could be performed at home (e.g. pregnancy test, glucose monitoring in diabetic patients), in hospital or the physician's office on a point of care device (e.g. hemoglobin, blood gases, lactate, electrolytes) or at the department of clinical chemistry where broad panels of routine biochemical markers or highly specialized single biochemical markers are analysed on huge automatized equipment.

In many aspects the department of clinical chemistry is superior when it comes to moderately quick and cost effective analysis. However in some situations lack of time, lack of appropriate amount of body fluid needed for analysis or the localisation (e.g. at home or when medical care is given at a significant distance from the department of clinical chemistry) excludes the department of clinical chemistry as a possible way to perform the needed analysis. In these situations some kind of point of care (POC) device is the most effective, or sole, solution to insure safe medical care for the individual patient. POC is the generic word for medical care that could be performed where the patient is located. When it comes to POC in-vitro diagnostic devices for analysis of one or several biochemical markers in a specific body fluid from a patient a broad spectrum of technical solutions are commercially available. The simplest form of a POC in-vitro diagnostic device, in terms of how the result is presented to the user, could be exemplified by the pregnancy test where the presence of the hormone human chorionic gonadotropin (HCG) in urine will be shown as a colour, a line or a "plus" sign. Much more advanced are the different analysing equipments, the size of huge microwave ovens, where many of the analyses performed at the department of clinical chemistry could be analysed point-of-care.

When it comes to POC technology the medical care giver has to do a trade-off between simple-to-use qualitative devices like the urine dipstick and the expensive, hefty but sophisticated lab-on-a-bench equipment giving full quantitative results on most of the biochemical analysis needed in modern medical care.

Numerous systems have been suggested to minimise one or more of the problems mentioned above. For instance, U.S. 2006/0222567 suggests the use of a mobile device, having a specifically designed accessory and a specific software to provide the ability of analysing a test in situ, i.e. to more or less instantly may display a test result. However, this solution presents some disadvantages, e.g. that it requires specific accessories, which most likely will be very costly. Furthermore, it may also be a disadvantage that it requires a mobile device having a relatively large processor capacity to run the program and the need of actually installing the program on each one of said mobile units. In its preferred form U.S. 2006/0222567 uses a digital picture, taken by the mobile unit, that is processed, i.e. regarding colour (change/intensity) to determine the test result. This may imply some requirements/restrictions on the equipment and the software that may not always be accomplished. Furthermore it may require the use of undesirably costly substances to obtain a sufficiently distinct colour change for the testing.

BRIEF SUMMARY

The object of the invention is to improve upon the situation described above which is achieved by means of the method as defined in claim 1. Thanks to the invention a much easier and more reliable testing may be performed. Furthermore it may facilitate the use of easily accessible equipment (less sophisticated equipment than normally used hitherto) to actually determine a diagnostic result. Indeed it also may drastically improve the possibility of visually determining if a certain diagnostic result may exist or not, i.e. without any need of auxiliary equipment.

According to a further aspect of the invention it is combined with a testing system arrangement, which further improves for a user, and which preferably presents at least two separate reference surfaces, preferably three, arranged to enable determination by said software that correct assessment of colour is achieved. Thanks to this aspect improved reliability may be achieved, because by the use of a plurality of reference surfaces the software may be used to compare the different reference surfaces to determine that the correct reference colour is chosen. Moreover the geometry of the reference surfaces, which is known by the software, may be used to control correct positioning of the mobile unit at the time of capturing a desired image.

As is evident a variety of different mobile units may be used to capture a desired image, e.g. scanners, video recorders, digital cameras, etc. and that therefore the use of the expression digital camera in the following shall not be given any limited interpretation, since it is evident that many different means may be used to fulfil the basic need, i.e. a digital image of sufficient quality to facilitate the desired image processing.

According to a further aspect to the system arrangement the testing may easily be performed by means of a mobile unit, preferably a smartphone equipped with a digital camera, simply by capturing a digital image of the testing device and transmitting that picture to a server which instantly performs the analyses and returns a diagnostic result to the mobile unit. Thanks to this solution there is no need for any large processing capacity in the mobile unit nor the use of any supplementary equipment, since the program executed at the server may handle test results from any source, due to the fact that the disposable testing device is arranged with a reference surface having a predefined colour setting, that the server uses as base reference to determine any possible colour change within the test area.

The invention described offers a solution making it possible to use an inexpensive disposable test device (that on its own may provide a binary "positive or negative" test) that, when needed, together with e.g. a smart phone will give the care giver instant clinically relevant quantitative and/or semi-quantitative test results at the point of care.

The disposable may contain specific reagents for one single biochemical marker or a panel of biochemical markers of interest for the specific situation. The reagents are preferably composed to give a visually detectable colour where the intensity of the colour, or change of colour, correlates with the concentration or activity of the biochemical marker/s of interest.

This could be exemplified by:
1. A combination of Lactate dehydrogenase and pH (increased hydrogen ion concentration) indicator for clinical use during or directly after delivery to determine if asphyxia severe enough to cause acidosis and cellular damage is present in the fetus/newborn.
2. Analysis of Lactate dehydrogenase alone or in combination with lactate, glucose, proteins in cerebrospinal fluid (CSF) for early detection of bacterial meningitis simultaneously with the lumbar puncture.
3. Analysis of the brain specific calcium binding protein s100b in urine for point-of-care detection of injury to the central nervous system e.g after asphyxia or trauma.
4. Creatinin analysis (using e.g. the Jaffés reaction) for instant decision support if a radiological examination could be performed without risk for renal failure.
5. Hemolysis detection (destruction of the red blood cells) which is a common source of error when occurring in-vitro and a sign of haemolytic disease if occurring in vivo. The disposables will use the red colour of hemoglobin in itself or by chemical means indicating the degree of hemolysis.
6. CRP analysis for instant indication if an infectious patient illness is caused by a virus or bacterial agents.
7. A combination of bilirubin, Amylases and CRP for triage assessment if the symptoms in a patient with abdominal pain are caused by pancreatic and/or bili-related ethology or not.

There is available microfluid technology where a chemical reaction for detection of a specific biochemical marker is coupled to a reagent giving a visual colour (WO2011/040874). The intensity of the colour correlates with the concentration of biochemical markers in the sample. However, small changes in colour are not possible to detect for the human eye. Also, if the biochemical marker have catalytic properties (enzymes) there is a risk that the same molecule will react multiple times giving a more explicit colour development as a function of the time delay between when the sample is mixed with the reagents and when the results is checked. These arguments will limit the use significantly both when the device is used on its own and the test result is visually checked but also if the colour change should be analysed with some kind of software (e.g. using a smart phone).

The limitations described could be minimized if another component is added to the assay. This component (from now called the inhibitor) may then be added to the existing assay with the purpose to block the biochemical marker up to a certain concentration, e.g. the upper normal limit of a specific biochemical marker. The inhibitor e.g. works through binding to the active site of the molecule and thereby prevent that the blocked biochemical marker-molecule is participating in the reaction coupled to the colour-change. The benefits are twofold: Firstly, specific reactions developing a very intensive colour reaction could be suppressed to optimize the possibility to detect change in colour with eye or software. Secondly, the inhibitor will stabilize the reaction and therefore prolong the time frame between when the sample is applied to the reagents and when the results should be checked. This would now be exemplified with the enzyme lactate dehydrogenase.

Lactate dehydrogenase (LDH) is a well-known biochemical marker of cellular damage seen in multiple critical conditions including severe asphyxia (lack of oxygen) during birth, ischemia in specific tissues (including gut and heart) and spread cancer.

In the cell LDH catalyse the reaction where pyruvate is converted to lactate, giving energy to the cell during anaerobic conditions (lack of oxygen. For example tetrazolium salt can be coupled to the reaction where NAD and lactate are substrates in the reaction and the activity of LDH will be reflected by a colour. The benefits from such a test would be that a process causing cell damage could be identified within minutes in a very small blood volume independently on the localisation of the patient. However the human eye will not be able to separate different LDH activates if they are too close to each other.

When such a colorimetric LDH test was assessed (e.g. by use of a device/method as described in WO2011/040874, herewith introduced by way of reference) by medical staff working at a delivery unit they did not have any difficulties deciding with the eye if an LDH activity was higher or lower when compared to a predetermined colour reference of 900 U/L if the difference was ≥300 U/L. When narrowing the difference to <200 U/L the ability to see this difference with the eye was significantly decreased. Also higher LDH activities (>1500 U/L) was difficult to distinguish from each other due to a very intense colour in this high LDH range.

When adding the inhibitor to the device all activity less than 900 U/L was "turned off" giving a change of colour only if the LDH activity exceeded this "cut off" of 900 U/L. by doing this the former continuous colour scale was now converted into a qualitative "high" or "low" LDH test. Also the intensity of colour in the higher LDH interval was less profound and therefore easier to assess.

When analysing the device with software, LDH activities in the intervals of 100 U/L (100, 200, 300 . . . 1400 U/L) was assessed using software on a smart phone. The colour developed on the LDH test was converted to the RGB colour model making it possible to distinguish all the LDH intervals from each other. In the higher LDH range (>1700 U/L) the RGB coordinates was closer to each other making the separation of the intervals more difficult to assess. With the use of inhibitor the clinical normal range was blocked. This principle will offer great benefits e.g. in home testing where all values within the normal range will be presented as "negative" or "low". Also the inhibitor causes a less profound colour reaction in the higher LDH range making it possible also to distinguish between different LDH intervals also in the higher LDH range.

According to another aspect of this invention it relates to simplified analysis of a test sample, e.g. using a change of colour (or certain colour, or colour intensity) to indicate a certain result. The main area relates to easy to handle, in-vitro diagnostic, point-of-care, portable and disposable test devices, to come to quick conclusions, e.g. to quickly detect if a patient suffers from a bacterial infection, severe perinatal asphyxia or cellular damage in one or several organ systems. The test device may include one or more chemical substances (the assay) that is allowed to react with a test sample (from the patient), which e.g. by means of a colour change indicates high levels of the biochemical marker. According to another aspect of this invention the biomarker to be measured in the test sample (from the patient) has an inherent colour and no chemical substances are needed. The colour intensity of the inherent colour correlates to the level of the biochemical marker.

There exist many such different testing devices. The big advantage is that they allow for testing, point-of-care, i.e. without using a laboratory, which also provides the big advantage that it is a very quick testing method. However, it is not always easy to determine if a (sufficient) colour change has occurred or not, e.g. it may require substantial training/experience.

According to one further aspect of the invention (that is not dependent on the use of an inhibitor, but which may be beneficially combined therewith) the colour of the test is determined by software, e.g. by means of electronically sending a photo/picture/scan of the test to a server, where exact determination of the colour may be established in real time. Preferably, a smart phone is used, which will enable the method to be easily implemented anywhere. The test device may have a body having a specific colour, that is used as reference when determining the colour change, which in its easiest form implies using a colour specific (e.g. white, plastic) body part, which encompasses the test compartment (having a transparent "window" or a soaked filter) where the colour change occurs. According to a further aspect there is provided means to enable a more easy/standardised manner of taking the picture.

BRIEF DESCRIPTION OF THE FIGURES

In the following the invention will be described in more detail with reference to the attached drawings, wherein.

DETAILED DESCRIPTION OF VARIOUS EMBODIMENTS

Figure 1:
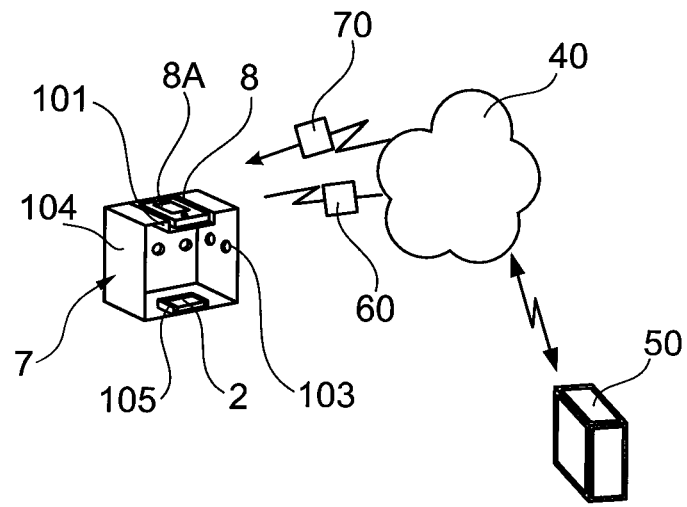
FIG. 1 schematically shows a preferred system according to the invention.
Figure 1A:
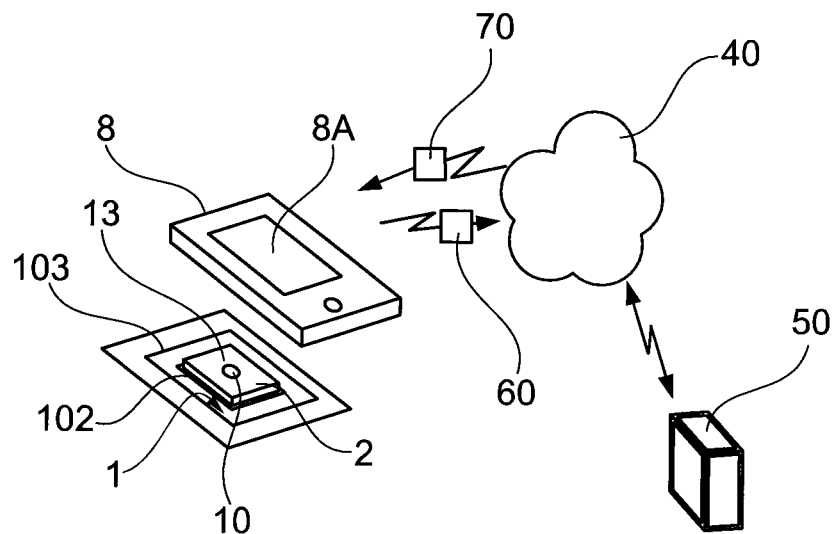
FIG. 1A. schematically shows a modified system according to the invention

In FIG. 1A there is schematically shown a testing system in accordance with the invention, wherein a mobile unit 8 with a digital camera, preferably a smart phone, e.g. an iPhone, is used to take a digital picture 60, of a test result presented in viewing area 10 of a disposable testing device 2. In its simplest form the user merely captures the digital picture, of the diagnostic device 2 without any other accessories than the mobile unit 8.

In another embodiment, see FIG. 1, there is used a different kind of template 1 in the form of a housing 104 with a first support surface 101 for the smart phone 8 and a second support surface 105 for the testing device 2.

The digital picture 60 captured by the mobile unit 8 is transmitted to a server 50 via any appropriate connection (depending on the place of the location), e.g. the internet 40. At the server 50 a specifically tailored software quickly runs a dedicated program to determine the outcome of the test and directly retransmits the result 70 to the mobile unit 8 where the test result is displayed on the display 8A of the mobile unit 8. Preferably the disposable testing device 2 is also equipped a unique code 13, e.g. printed, that is also captured in the picture, by means of which the software can determine what kind of testing device 2 the picture 60 relates to, and possibly also other desired aspects, e.g. stored in a memory connected to the server 50

Alternatively, the mobile unit 8 may be equipped with its own processor/software to have also the analysis performed in situ. In that case the software may also contain control features that assists the user to capture the image of the testing device, in accordance with a predetermined manner, e.g. to get the right angle and distance. This may for example be achieved by means of a triggering function in the software, that automatically captures the picture 60 if certain parameters are fulfilled (e.g. distance, angle) or (possibly in combination with the latter) by means of a aiming device in the display, that guides the user to position the mobile unit 8 in a desired position for taking the picture.

As presented in FIG. 1A there is shown a further embodiment for an the arrangement that may also be used in connection with other means to facilitate guidance for taking the picture 60, i.e., a relatively simple template 1, i.e. in connection with producing a digital picture 60 of a test result. The test result is presented in a viewing area of the disposable testing device 2. The template 1 is arranged with a marking 102 indicating a desired positioning of the disposable test device 2 on the template 1. In a preferred embodiment the template 1 has an outer configuration (or marked frame) 103 adapted to control a beneficial positioning of the mobile unit 8 during capturing of the picture. This may easily be achieved by designing the template with a frame 103 that correspond to the geometry of the camera display in the mobile unit 8, such that a desired/"correct" positioning (i.e. distance between the test device and camera lens) is achieved when the frame "fits" into the viewer of mobile unit 8. Thereby a kind of standardized illumination may be achieved when using the flash of the mobile unit 8. Hence a kind of standardized illumination may be obtained, by simply setting a desired frame for each kind of mobile unit, e.g. to provide more or less the same illumination by means of the built in flash of that mobile unit. Not merely, simply by controlling a desired distance, but also indeed assisting in controlling a desired direction of the flash, since the "frame" will also assist in positioning the mobile unit 8 in a desired angle/plane (e.g. parallelly) in relation to the plane of the template, which normally will be put on a horizontal surface. The template 1 (which preferably is made in a durable material, e.g. paper enclosed in plastic) may be equipped with a number of frames 103 (not shown) each one corresponding to a specific mobile unit 8, and may also be equipped with written instructions (e.g. on the back side)

Figure 2A:
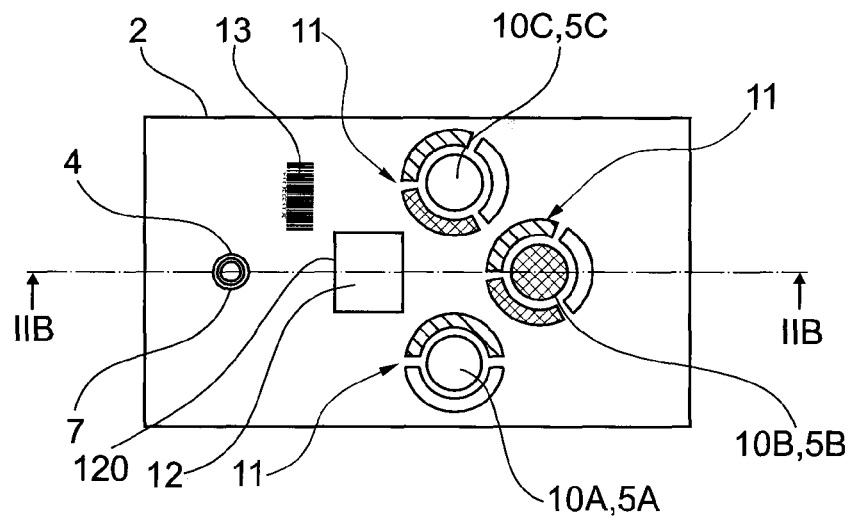
FIG. 2A shows a possible embodiment of a disposal testing device according to the invention, seen from above.

As shown in FIG. 2A the disposal test device 2 is arranged with one or more reference areas 12 having a colour that is exactly known by the server 50, implying that even if the digital picture 60, that is transmitted to the server 50, would be somehow distorted the software within the server 50 will be able to determine any possible colour change by knowing exactly the actual colour of that reference area 12. In the preferred embodiment the reference colour within the reference area 12 is the very same as the colour of the body of the disposable testing device 2, e.g. white plastic. This brings about several advantages, firstly that there will be no extra cost for producing a reference area 12 and furthermore that even if the reference area is scratched the very same colour will still be maintained since the whole body has the very same colour. In a preferred embodiment a protection foil (not shown) is applied onto the top surface of the testing device 2, which foil safeguards that no deposits will be present on the reference area 12, if maintained on until making the test.

Moreover the reference area may be on the support as long as it is captured in the same image as the test area.

Trials that have been performed indicate that in a digital picture 60 there is a good correlation between change of colour (due to different illumination) of the reference area 12, and the corresponding change of colour (of another kind/frequency) within a visible compartment 10, e.g. arranged with a transparent wall, or a "wall" interacting in the reaction, implying that correction/calibration is relatively easy to achieve by means of software, in accordance with the invention.

Figure 2B:
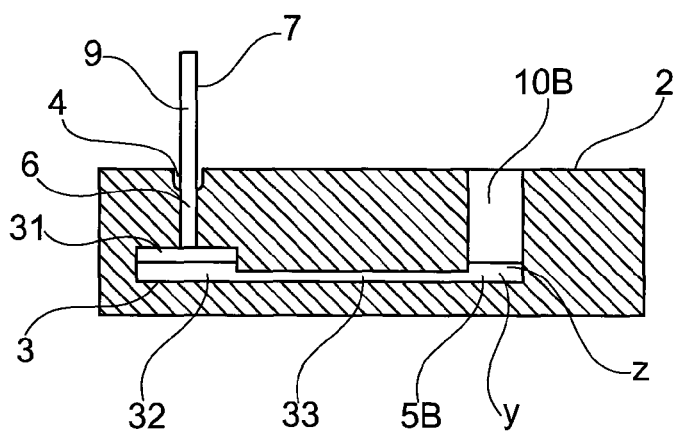
FIG. 2B shows a cross sectional view a long line II B-II B in FIG. 2A.

In FIGS. 2A-2B is presented an example of disposable device 2 according to the present invention with a sample inlet 4 in the form of a sample inlet connected to a chamber 6 adapted to receive a capillary device 7 containing a sample 9 arranged to be placed onto a receiving device, e.g. a plasma separation device 3. The sample inlet 4 is preferably surrounded by a funnel-like insertion pit for guiding a capillary sample collector 7 into chamber 6. Herein is further seen said optical viewing areas 10A-10C which allow for observing ongoing reaction inside detection compartments 5A-5B.

FIG. 2A is seen from a planar top-view, and FIG. 2B is a cross-view according to IIB in FIG. 2A. Herein device 2 is supplied with test blood 9 by means of a capillary device 7 being filled with the sample, e.g. a whole blood amounting to, e.g. about 50 µL. Depending on the patient and/or on the particular design of device 2 (e.g. number of detecting compartments, size of the channels etc.) various amounts of blood sample are imaginable, and it is possible to use as little as 1 µL, or as much as 100 µL, a preferred amount being between 25-75 µL.

In order to facilitate insertion of sample the area around sample inlet 4 is preferably pitted for guiding capillary device 7 into chamber 6. In FIG. 2A the capillary device 7 has already been inserted into a compartment 6 of the cartridge 2 to interface the blood sample 9 with the cartridge 2 and placing the blood sample 9 onto the filter 31 of the plasma separation device 3. Instead of a capillary device 7 it is conceivable to provide the sample 9 by means of a pipette releasing a drop of sample onto a marked area on the cartridge 2. A negative pressure is manually generated (or by means of a passive filter, or by means of capillary force) and plasma is urged through the filter 31 and into plasma collection chamber 32 wherefrom it proceeds through microfluidic channel 33 and is distributed into different detection compartments 5A-C. As is seen in FIG. 2B the testing system comprises optical viewing areas 10B in that at least the portions 10A-C of the disposable device 2 above each detection compartment 5B is transparent, meaning each detection compartment 5B is visible and can be observed during ongoing reaction.

Each detection compartment 5 A-C, forms an encapsulated unit, which besides of enabling merely filtered fluid to enter, also provides the advantage that the volume of the biological sample that is put in contact with the reagent is known. As is evident for the skilled person this known input data (volume) may be of essence in determining the output and to optimize conditions. Furthermore, in connection with blood, it is known that the amount of plasma may vary a lot from individual to individual, i.e. even if the same volume of blood is applied at the inlet a big variation of filtered amount of plasma may be obtained. In the preferred embodiment the volume within a compartment 5 A-C is in the range 0.1-15 µl, more preferred 3-10 µl, and most preferred 4-9 µl.

The separation filter can be of different types, exemplified but not limited to, blood separation filters, filters for separation by size, filters for affinity, capture or binding of specific components in the fluid to be filtered. The filters may be made of natural or synthetic material, or a combination thereof, and be of symmetric or asymmetric type. The separation can be performed by inducing a subpressure or by capillary means.

Each detection compartment 5A-C is prepared with a reagent composition Y, preferably of different kind in each compartment, e.g. arranged to react with one of the following biochemical markers: Hb, LDH, aspartate aminotransferase (AST), alanine aminotransferase (ALT), lactate, Creatinine Kinase (CK), Creatinine, Amylasis (PIA), C-reactive protein (CRP), Hydrogen ion concentration (pH), Albumin, K, Mg and Ca. Preferably each device 2 comprises at least two detection compartments 5A-B for detecting Hb and LDH respectively, and optionally one or more detection compartment for detection of one or more of AST, ALT, lactate, CK, Amylasis K, Mg and Ca. It is to be understood that the examples mentioned above are by no means limiting to the basic principles of the invention.

Moreover another component Z may be added to the reagent composition or added to the test sample before it reaches the compartment of at least one compartment 5A-C. This component Z (from now called the inhibitor) is added to the composition Y with the purpose to block the biochemical marker up to a certain concentration, e.g. the upper normal limit of a specific biochemical marker. The inhibitor Z works through binding to the active site of the molecule and thereby prevent that the blocked biochemical marker-molecule is participating in the reaction coupled to the colour-change. The benefits are twofold: Firstly, specific reactions developing a very intensive colour reaction could be suppressed to optimize the possibility to detect change in colour with eye or software. Secondly, the inhibitor Z will stabilize the reaction and therefore prolong the time frame between when the sample is applied to the reagents and when the results should be checked.

After a predetermined time-span (e.g. after the reaction may have been interrupted by a reaction stopper) any colour-shift is visually detected by the user of the testing system 1. The total time from applying the blood sample 9 in 2A to determine test result in 2C is less than 10 minutes, but preferably less than 5 minutes and more preferred within one minute.

FIG. 2A presents a planar view of the testing system after that a possible reaction has taken place within detection compartments 5A-C. In order to determine the level of biochemical markers the colour shift (if any) in each detection compartment 5A-C is compared to a standard reference interval which is preferably provided together with the testing system. According to one embodiment of the invention the area next to each detection compartment 5A-C is provided with a number of reference colours 11 whereby assessment of marker-level is easily performed. Here, detection compartment 5A is arranged to determine presence of Hb, and 5B-C are arranged to determine or estimate levels of any other biochemical marker. When using the test card solely on a biochemical marker with known cut off between normal and abnormal this cut off could be shown as a colour reference if the developed colour/s in the detection well/s is more intense than the colour reference the test is positive. The adding of an inhibitor will make it possible to take away all the colour if the biomarker of interest is low and only present a visual colour if the cut off (the amount of inhibitor) is exceeded. However when using the inhibitor for colour modification (e.g. to decrease the intensity of a colour in high concentrations of a biochemical marker) it could be used together with a colour reference. However, when the test card is used together with a soft ware device the colour references is not necessary due to the fact that the concentration of the biochemical marker will be presented as interval data or continuous values in the software.

For instance in FIG. 2A a situation is exemplified where no colour-shift has occurred in the compartment for Hb 5A, indicating that the test is valid. A reaction has occurred in compartment 5B, which colour-shift corresponds to one of given reference colours 11, whereas no notable reaction has occurred in compartments 5C. Preferably a user of a testing system 1 is instructed to react if colour-shift has resulted in a certain colour intensity. Such instructions may be marked in connection to the reference interval, for instance in the form of a symbol indicating the parts of reference interval representing risk of hypoxia.

In FIG. 2A the standard reference 11 for compartments 5B-C has three colour sections, however a person skilled in the art will understand that this is in no way limiting regarding the invention.

Figure 3:
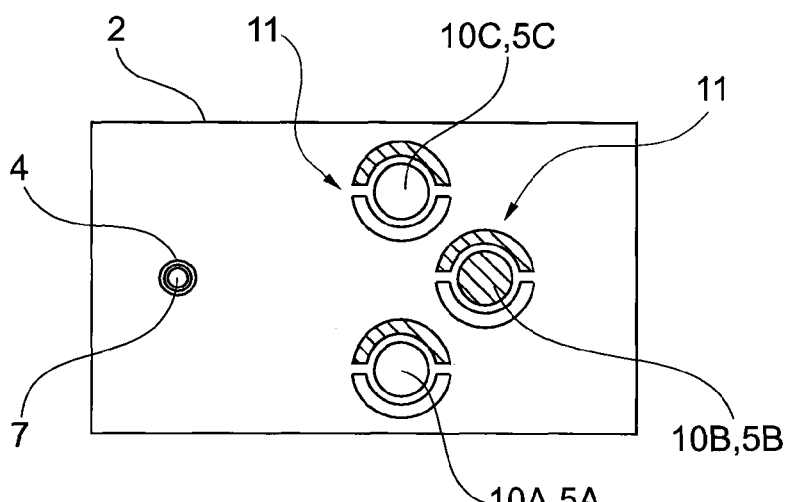
FIG. 3 shows a further example of a disposable test device in accordance with the invention.

Yet another example of possible reference interval 11 is seen in FIG. 3 where a standard reference 11 has only two colour sections, meaning a reading will provide a user with a positive or a negative answer only. Such a design of a reference standard is suitable in medical situations where it is possible to present a concentration limit above which it is always required to take medical action, or in situations where a simple and fast reading is more important than a quantitatively precise measurement of the marker level.

Thanks to the use of an inhibitor Z it may be significantly easier to distinguish between different intervals, i.e. identify/determine a test result, than according to conventional methods.

Moreover the test can be of lateral flow type comprising antibodies or of type similar to urine dipsticks where the sample is not guided.

The skilled person realizes that a large variety of modifications may be performed without the use of inventive skill, departing from the description above, e.g. the use of glass or some other suitable material in place of plastic etc. For instance, instead of directly capturing one digital image, it is foreseen that instead a video may be recorded and that either the software within the mobile unit 8 (or within a server) analysis the colour by means of the plurality of "images" of the video, or that the software automatically chooses one of the images (fulfilling certain criteria) for performing the analysis. Furthermore it is within the scope of the present invention to use housing for capturing the digital picture 60, with a first support unit adapted to correctly position the disposable test device in a desired position within the housing, preferably at the bottom thereof, and at the opposite side of the housing, at the top thereof, a second supporting unit for correct positioning of the mobile unit, having its camera lens directed towards the testing device. The mobile unit may then be locked in its position within the second supporting unit, to eliminate possible theft and also to facilitate easy and quick use of the equipment without any need of adjustments. Moreover the housing may be arranged with an appropriate set of lights, to provide the disposable test device with an appropriate illumination at the time of taking the picture. Of course the lights may be omitted, to instead use the internal flash of the mobile unit.

Many modifications and other embodiments of the inventions set forth herein will come to mind to one skilled in the art to which these inventions pertain having the benefit of the teachings presented in the foregoing descriptions and the associated drawings. For example it is evident for the skilled person that the disposable device 2 may have a sample inlet 4 adapted to receive a sample without the use of capillary device 7, e.g. to receive a drop of blood directly from a finger. Further, it is evident for the skilled person that also other fluids, dispersed stool, etc., may be used in connection with the invention. Moreover, it is foreseen that the inlet 4, as understood in connection with the invention may be in different forms, e.g. in the form of a discrete opening as presented in the figures, or in the form of a relatively large "inlet surface", e.g. a soaking layer attached to the card. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. For instance the mentioning of "server" shall not be construed in a limiting manner, but instead that the term server, as used in the context, refers to an arrangement wherein remotely positioned capacity (e.g. processing capacity, memory capacity, support capacity, etc.) is being used, i.e. encompassing any different kind of "server-setups", e.g. server-client models, peer to peer models, etc., and/or combinations thereof. Moreover it is evident that the "server" functionality may also be used to link the result to the medical record of an individual patient, e.g. by applying a sticker containing a patient identifier on the disposable device 2, before capturing the image, to enable the software to identify the patient. Further functionality within the server system may be used to achieve automatic reordering of disposables 2, when a certain number has been consumed, etc.

The invention claimed is:

1. Testing system for assessing the level of a biochemical marker, said system comprising:
   a disposable device (2) comprising a sample inlet (4) and at least one visible detection compartment (5A, 5B), wherein:
   at least one of said compartments (5A, 5B) contains a composition comprising a chemical means (Y) for direct detection of said biochemical marker; and
   said composition further comprises an inhibitor (Z) arranged within said at least one of said compartments (5A, 5B), said inhibitor being arranged to block the biochemical marker up to a certain concentration.

2. Testing system according to claim 1, wherein said system further comprises a separation filter (31) that is positioned between said inlet (4) and said detection compartment (5A, 5B).

3. Testing system according to claim 1, wherein on said disposable device (2) there is arranged at least one reference surface (12) configured to enable determination by said software that correct assessment of color is achieved.

4. Testing system according to claim 2, wherein said at least one reference surface (12) comprises at least two separate reference surfaces (12) configured to enable determination by said software that correct assessment of color is achieved.

5. Testing system according to claim 2, wherein said at least one reference surface (12) comprises at least three separate reference surfaces (12) configured to enable determination by said software that correct assessment of color is achieved.

6. Testing system according to claim 2, wherein there are at least two visible detection compartments (5A, 5B), wherein one is arranged for determining whether the amount of hemoglobin (Hb) in a sample of body fluid exceeds a predetermined level.

7. Testing system according to any of claim 1, wherein said sample is at least one of plasma, serum, urine, cerebrospinal fluid (CSF), intra-peritoneal fluid, or saliva.

8. Testing system according to claim 1, wherein:
the disposable device (2) comprises more than two visible detection compartments (5A-C) arranged on the card; and
each one of said compartments is configured with chemical means in the form of a reagent composition.

9. Testing system according to claim 1, wherein at least one of said chemical means or said composition is in the form of at least one of a dry chemical means or a wet chemical means.

10. Testing system according to claim 1, wherein:
said disposable device (2) is used in an arrangement for detection of said biochemical marker; and
said arrangement comprises a mobile unit (8) including a digital camera configured to capture a digital picture (60) of said at least one visible detection compartment (5A, 5B), software run on a processor for analyzing said picture (60) to assess said level, and means configured to present the result (70) of said assessment in a display (8A) at least one of on or connected to said mobile unit (8).

11. Testing system according to claim 10, wherein said disposable device (2) is arranged with at least one reference surface (12) having a predetermined color setting that is known to said software to enable exact assessment of the color within said detection compartment (5A, 5B) by the use of said reference surface (12) within said digital picture as a basis reference.

12. Testing system, according to claim 1, wherein an identifier (13) is further provided on said disposable device (2), said identifier (13) being configured to enable identification predetermined aspects regarding each individual disposable device (2).

13. Method for assessing the level of a biochemical marker, said method comprising the steps of:
providing a disposable device (2) with a sample inlet (4) and at least one visible detection compartment (5A, 5B);
arranging said device (2) with a composition including a chemical means (Y) for direct detection of said biochemical marker, said composition being located in at least one of said compartments (5A, 5B); and
providing said composition to also include an inhibitor (Z) within said at least one of said detection compartments (5A, 5B), said inhibitor (Z) being arranged to block the biochemical marker up to a certain concentration.

14. Method according to claim 13, wherein said method further comprises the step of providing a separation filter (31) between said inlet (4) and said detection compartment (5A, 5B).

15. Method according to claim 13, further comprising the step of providing on said disposable device (2) at least one reference surface (12) configured to enable determination by said software that correct assessment of color is achieved.

16. Method according to claim 13, wherein there are provided at least two visible detection compartments (5A, 5B), wherein one is arranged for determining whether the amount of hemoglobin (Hb) in a sample of body fluid exceeds a predetermined level.

17. Method according to claim 13, wherein said sample is at least one of plasma, serum, urine, cerebrospinal fluid (CSF), intra-peritoneal fluid, or saliva.

18. Method according to claim 13, wherein:
the disposable device (2) comprises more than two visible detection compartments (5A-C); and
each one of said compartments is arranged with chemical means in the form of a reagent composition.

19. Method, according to claim 13, further comprising the step of enabling identification of predetermined aspects regarding each individual disposable device (2), said identification being performed by using an identifier (13) on said disposable device (2).

20. Method, according claim 13, further comprising the step of arranging the inhibitor (Z) to get in contact with the test sample before entering the detection compartment (5A, 5B).

* * * * *